(12) United States Patent
Przepasniak et al.

(10) Patent No.: US 7,514,591 B2
(45) Date of Patent: *Apr. 7, 2009

(54) INTERLABIAL ABSORBENT ARTICLE WITH IMPROVED FLUSHABILITY CHARACTERISTICS

(75) Inventors: Ann Marie Przepasniak, Appleton, WI (US); Susan M. Weyenberg, Appleton, WI (US); Patricia A. Mitchler, Neenah, WI (US); Heather A. Sorebo, Neenah, WI (US); Wilfred E. Riddell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 69 days.

This patent is subject to a terminal disclaimer.

(21) Appl. No.: 10/732,827

(22) Filed: Dec. 10, 2003

(65) Prior Publication Data

US 2005/0148959 A1    Jul. 7, 2005

(51) Int. Cl.
*A61F 13/15* (2006.01)
(52) U.S. Cl. .................. 604/358; 604/385.17; 604/378; 604/385.01; 604/385.23; 604/381; 604/365; 604/367
(58) Field of Classification Search ................. 604/358, 604/378, 385.01, 385.17, 385.23, 381, 365, 604/367
See application file for complete search history.

(56) References Cited

U.S. PATENT DOCUMENTS

| 3,420,235 A | 1/1969 | Harmon |
|---|---|---|
| 3,726,277 A | 4/1973 | Hirschman |
| 3,891,584 A | 6/1975 | Ray-Chaudhuri et al. |
| 3,983,873 A | 10/1976 | Hirschman |
| 4,175,561 A | 11/1979 | Hirschman |
| 4,341,217 A | 7/1982 | Ferguson et al. |
| 4,522,967 A | 6/1985 | Sheldon et al. |
| 4,600,404 A | 7/1986 | Sheldon et al. |
| 5,429,631 A | 7/1995 | Grenier |
| 5,460,624 A | 10/1995 | Ahr et al. |
| 5,484,429 A | 1/1996 | Vukos et al. |

(Continued)

FOREIGN PATENT DOCUMENTS

EP    0161663    11/1985

(Continued)

OTHER PUBLICATIONS

EPO Search Report, Dec. 2, 2004.
U.S. Appl. No. 10/732,163, filed Dec. 10, 2003.

*Primary Examiner*—Tatyana Zalukaeva
*Assistant Examiner*—Ginger T Chapman
(74) *Attorney, Agent, or Firm*—Dority & Manning, P.A.

(57) ABSTRACT

An interlabial absorbent article configured for disposition primarily within the vestibule of a female wearer includes a generally liquid permeable cover sheet, a generally liquid impermeable back sheet, and an absorbent material disposed between the cover sheet and the back sheet. The back sheet has a water vapor transmission rate that is at least about 20% of a water vapor transmission rate of the cover sheet. The cover sheet and said back sheet may have a contact angle mismatch of less than about 25%. The absorbent material may have a density greater than water. Upon being flushed, the article has an initial neutral buoyancy and subsequently sinks within about 7 days from being flushed.

16 Claims, 2 Drawing Sheets

U.S. PATENT DOCUMENTS

| | | | |
|---|---|---|---|
| 5,509,913 A | 4/1996 | Yeo | |
| 5,573,523 A | 11/1996 | Whalen et al. | |
| 5,605,764 A | 2/1997 | Miller et al. | |
| 5,613,964 A | 3/1997 | Grenier | |
| 5,681,299 A | 10/1997 | Brown | |
| 5,693,707 A | 12/1997 | Cheng et al. | |
| 5,762,644 A | 6/1998 | Osborn, III et al. | |
| 5,891,126 A | 4/1999 | Osborn, III et al. | |
| 5,948,710 A | 9/1999 | Pomplun et al. | |
| 5,952,251 A | 9/1999 | Jackson et al. | |
| 6,033,391 A | 3/2000 | Osborn, III et al. | |
| 6,063,858 A | 5/2000 | Daniels et al. | |
| 6,171,292 B1 | 1/2001 | Osborn, III et al. | |
| 6,183,456 B1 | 2/2001 | Brown et al. | |
| 6,203,512 B1 | 3/2001 | Farris et al. | |
| 6,232,521 B1 * | 5/2001 | Bewick-Sonntag et al. | 604/378 |
| 6,270,486 B1 | 8/2001 | Brown et al. | |
| 6,514,602 B1 | 2/2003 | Zhao et al. | |
| 6,663,611 B2 * | 12/2003 | Blaney et al. | 604/385.01 |
| 6,776,947 B2 * | 8/2004 | Brady et al. | 264/210.2 |
| 7,138,560 B2 * | 11/2006 | Przepasniak et al. | 604/364 |
| 2001/0000796 A1 | 5/2001 | Osborn, III et al. | |
| 2001/0001815 A1 | 5/2001 | Osborn, III et al. | |
| 2001/0025163 A1 | 9/2001 | Brown et al. | |
| 2002/0040213 A1 * | 4/2002 | Tweddell, III et al. | 604/385.01 |
| 2002/0058921 A1 | 5/2002 | Sigl | |
| 2003/0225388 A1 | 12/2003 | Bhavani | |
| 2004/0018366 A1 | 1/2004 | George et al. | |
| 2004/0019168 A1 | 1/2004 | Soerens et al. | |
| 2004/0043688 A1 | 3/2004 | Soerens et al. | |
| 2004/0122402 A1 | 6/2004 | McDaniel | |
| 2004/0122403 A1 * | 6/2004 | Mitchler et al. | 604/385.17 |

FOREIGN PATENT DOCUMENTS

| | | |
|---|---|---|
| EP | 0781538 | 7/1997 |
| EP | 0835337 | 10/2001 |
| EP | 0989837 | 4/2002 |
| WO | 9518191 | 7/1995 |
| WO | 9808475 | 3/1998 |
| WO | 9926574 | 6/1999 |
| WO | 9956689 | 11/1999 |
| WO | 0166160 | 9/2001 |
| WO | 2004 011046 A1 | 2/2004 |
| WO | 2004 060248 A1 | 7/2004 |

* cited by examiner

INTERLABIAL ABSORBENT ARTICLE WITH IMPROVED FLUSHABILITY CHARACTERISTICS

FIELD OF THE INVENTION

The present invention relates to the field of feminine hygiene products, and more particularly to interlabial absorbent articles.

BACKGROUND

A broad range and wide variety of absorbent articles configured for absorption of bodily exudates such as menstrual fluid are well known. With respect to feminine hygiene, the art has offered two basic types of feminine hygiene protection: namely sanitary napkins and panty liners, developed for external wear about the pudendum region, and tampons, developed for placement within the vaginal cavity, and accordingly for interruption of menstrual flow therefrom prior to such menstrual flow reaching the vestibule. Hybrid feminine hygiene protection devices, attempting to merge the structural features of both sanitary napkins and tampons in a single type of device, have also been proposed, but have not seen a meaningful measure of acceptance.

Other less intrusive devices, known as labial or interlabial devices or pads, have also been proposed. These articles are designed to reside primarily within the wearer's vestibule while having a portion residing at least partially external of the wearer's vestibule. Interlabial articles can provide a preferred profile of appearance when viewed through a wearer's outer garments and do not have the same problem of reliance on swelling within the vaginal canal as required by tampons. U.S. Pat. Nos. 5,484,429; 4,175,561; 3,983,873; and 3,726,277 disclose various types of interlabial absorbent articles.

Interlabial absorbent articles are generally designed to be expelled by the urine stream when the wearer urinates. The article thus falls into a toilet fixture where it can be flushed. The relatively small size of interlabial devices facilitates flushing into conventional sewer and septic systems. However, care must still be taken that the articles do not obstruct or otherwise damage the sewer or septic system. A solution suggested in the art is to design the articles to be readily dispersible in water and, in this regard, efforts have been made in the art to provide interlabial articles that dissipate or disperse quickly in water. For example, U.S. Pat. No. 6,171,292 B1 describes an interlabial absorbent article that is designed so that the components of the article fragment within at least two hours of exposure to mildly agitated room temperature water. Alternately, the components may separate from each other without themselves fragmenting. The '292 patent teaches that it would be most preferred if the article fragmented within about 15 minutes. U.S. Pat. No. 5,573,523 describes a biodegradable and flushable mini-pad formed entirely of cellulosic materials. The outer panels are mechanically bonded at their perimeters without an adhesive to enhance biodegradation of the pad.

However, the desire for an interlabial absorbent article that disperses quickly in water may conflict with performance requirements for the article. Due to the relatively high water content of viscous and vaginal fluids, use of a water soluble adhesive (or no adhesive at all) that immediately starts to dissolve and cause the article to break up could sacrifice the seal strength and product integrity while in use. Wearing time and efficiency of the product may also be reduced if the article tends to break apart prior to being expelled upon urination as intended. Absorbent articles that tend to fragment into individual components before or during flushing may also tend to cause clogging of a structure's plumbing system if misalignment or natural obstructions exist. The more components or articles that "travel" through a home's contorted plumbing system per absorbent article flushed increases the risk that any one such component may become entrapped or entangled on obstructions, roots or the like, as compared to a single intact article.

Thus, a need exists for an interlabial absorbent article design that offers the benefits of a dispersible product without sacrificing performance of the article or adding to the risk of plumbing clogs or other problems upon flushing the article.

SUMMARY

Objects and advantages of the invention will be set forth in part in the following description, or may be obvious from the description, or may be learned through practice of the invention.

The present invention relates to a unique configuration for a feminine care interlabial absorbent article that offers distinct advantages over conventional devices. The interlabial absorbent article includes unique combinations of materials to produce an initial generally neutral buoyancy and delayed sinking properties that result in safe transport of the intact article through plumbing and municipal systems. The articles do not substantially disperse or break apart during transport, and preferably sink within about 7 days after being flushed. Sinking within 7 days minimizes chances of the product becoming clogged in piping and septic tanks and from requiring removal from water treatment plants.

Even if the articles do not sink within 7 days, the neutral buoyancy characteristic of the articles alone adds significant benefit. Neutral buoyancy tends to prevent the articles from floating on the surface of the water stream and being forced over the tank baffle into the second chamber of conventional septic tanks with the effluent where they may be subsequently pumped or flow by gravity into the drain field or possibly clog the system outlet resulting in a back-up of the system. In a waste treatment facility, neutrally buoyant articles will be intercepted by the screens or grinders prior to entering the water purification process.

Maintaining neutral buoyancy allows the article to essentially ride or "skim" near the top surface of the water while traveling through the toilet system, through a structure's lateral piping system, and out to the sewer stream without clogging in any of these systems. As the product travels to the sewer stream or septic tank and suspended solid particles begin to collect on the article, the article begins to travel between the bottom of the pipe and the water/air stream above it. Over time, the article should become negatively buoyant and sink to the bottom of the septic tank or to the bottom of the clarifying tank at the waste water treatment plant.

Eventual sinking of the article provides distinct advantages. First, as mentioned above, sinking prevents the article from being carried into a septic tank's second chamber and possibly out to the drain field. Sinking the article to the bottom of the septic tank provides an opportunity for anaerobic degradation of the natural materials, such as a rayon cover or absorbent, or cotton absorbent. Sinking of the product also reduces the chances of the product being observed intact by municipal water treatment employees, or homeowners.

In an embodiment according to the invention, the interlabial article includes a generally liquid permeable cover sheet, a generally liquid impermeable back sheet, and an absorbent material disposed between the cover sheet and the back sheet. The back sheet has a water vapor transmission rate that is at least about 20% of a water vapor transmission rate of the cover sheet, and the cover sheet and the back sheet have a contact angle mismatch of less than about 25%.

In a particular embodiment, the cover sheet has a water vapor transmission rate of at least about 30,000 Mocon value. For example, the cover sheet may be a spunlace laminate material having a water vapor transmission rate of about 40,000 Mocon value. This spunlace material material may comprise a rayon and film combination having a Mocon value of about 39,500, for example about 39,950

In still another embodiment, the cover sheet may have a water vapor transmission rate of at least about 50,000 Mocon. For example, the cover sheet may be a bonded carded web material having a Mocon value of about 52,500, for example about 52,612.

The back sheet may be, for example, a highly breathable stretch thermal laminate (HBSTL) material having a water vapor transmission rate of at least about 10,000 Mocon value.

To aid in eventual sinking of the article, the absorbent material may have a dry density of at least about 1.0 g/cc. Alternately, the absorbent material may have a wet density of at least about 1.0 g/cc.

It may be desirable that the article remain intact during flushing and transport through a septic system or municipal sewage plant. In this regard, a suitable adhesive may be disposed around a circumference of article and in an amount such that the article does not separate into individual components for at least about 7 days after being flushed.

Aspects of the invention will be described in greater detail below by reference to embodiments illustrated in the attached drawings.

DETAILED DESCRIPTION

Reference will now be made in detail to embodiments of the invention, one or more examples of which are illustrated in the drawings. Each embodiment is for purposes of explaining the invention, and not meant as a limitation of the invention. For example, features illustrated or described as part of one embodiment may be used with another embodiment to yield still a further embodiment. It is intended that the present invention include these and other modifications and variations as come within the scope and spirit of the invention.

As used herein the term "dispersible" means that the fibers of a material are capable of debonding, resulting in the material breaking down into smaller pieces than the original sheet. Debonding is generally a physical change of scattering or separation, as compared to a state change, such as dissolving, wherein the material goes into solution, e.g., a water soluble polymer dissolving in water.

As used herein, the term "flushable" means that an article, when flushed down a conventional toilet fixture containing approximately room temperature water, will pass through the fixture, in-house plumbing, and the sewer lateral (i.e., the piping between the house or building and the main sewer line) without clogging.

As used herein, the term "interlabial absorbent article" refers to a device having at least one absorbent component, and which is specifically configured for disposition between the labia majora, extending at least partially. into the vestibule of a female wearer during use. The vestibule is considered to be the region defined within the labia beginning at about a point lying caudally from the anterior labial commissure and extending rearward to the posterior labial commissure, and bounded inwardly by the floor of the vestibule. One of skill in the art fully understands that there is a wide range of variation among women with respect to the relative size and shape of labia majora and labia minora as the same interrelatedly define the contour of the vestibule. For purposes of the present description, however, such differences will not specifically be addressed, it being recognized that in any event the disposition of the absorbent article into the vestibule necessitates placement between the labia majora regardless of any such consideration respecting the labia minora. An interlabial absorbent article is disposed at least partially within the vestibule for partially occluding the vestibule with respect to fluid flow from the vestibule. In this regard, the predominant use of the absorbent article is for the absorption of menstrual or intermenstrual fluid emitted via the vaginal orifice, although the article is equally well adapted to serve as a type of incontinence device for absorption of urine as occurs upon minor, female incontinence.

As used herein, the term "neutral buoyancy" refers to a body's ability to maintain a buoyant position in water without floating to the surface or sinking. Some objects, when placed in water, are positively buoyant and float to the surface. Other objects are negatively buoyant and sink. Neutrally buoyant objects neither float nor sink over the short term.

The present invention provides an interlabial absorbent article configured for disposition primarily within the vestibule of a female wearer. The article may take on any suitable overall shape and configuration, and is illustrated in the figures as a simple oval shape for explanation purposes only. The article includes a liquid and vapor permeable cover sheet, a back sheet that is at least vapor permeable and may also be liquid permeable, and an absorbent material disposed between the cover sheet and back sheet that has a density greater than sewage effluent (typically water). Certain combinations of materials used for these components provide the desired flushability characteristics of articles according to the invention, as described in detail below. The individual components may be held together by conventional techniques to form the article. For example, a construction adhesive may be used to retain the components together as a coherent unit with the cover sheet and back sheet sealed around a circumference of the article. The cover sheet and back sheet may be joined to at least a portion of the absorbent material. The adhesive may be formulated to ensure that the article does not disperse or fragment into individual components for at least about 7 days after the article is exposed to an aqueous environment, for example after being dropped into a toilet and flushed. Alternatively, the components may be bonded together using any convention bonding technique, such as thermal bonding, ultrasonic or sonic bonding, and so forth.

Various advantages may be achieved with an interlabial absorbent article according to the invention. For example, the product may be used for an extended period under conditions where it is exposed to bodily fluids having a high water content without worry that the product will prematurely fail either by coming apart or causing premature leakage because of poor product integrity. The article can be readily flushed and, because of its neutral buoyancy, will be conveyed after flushing through a structure's plumbing system as a single component without becoming clogged in a system's piping or septic tank. After about 7 days, the article will sink in the septic tank. In the clarifying tank of a waste water treatment plant, the product will sink much quicker, for example within hours.

Figure 1:
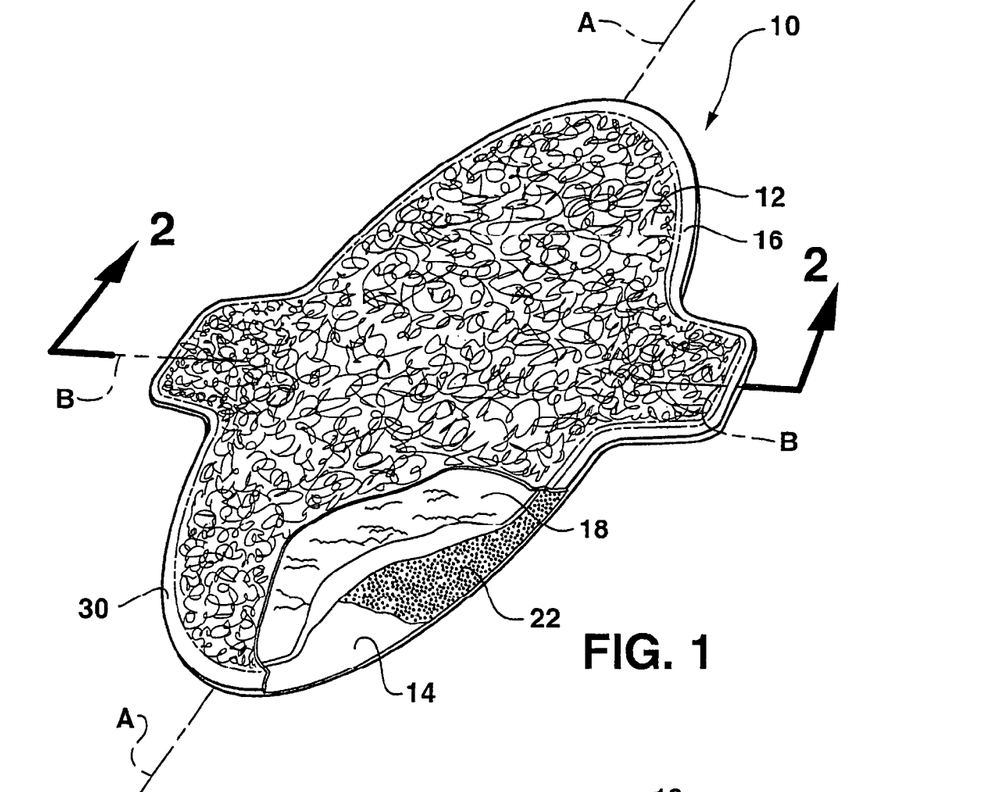
FIG. 1 is a perspective and partial cut-away view of an interlabial absorbent article in accordance with the invention.
Figure 2:
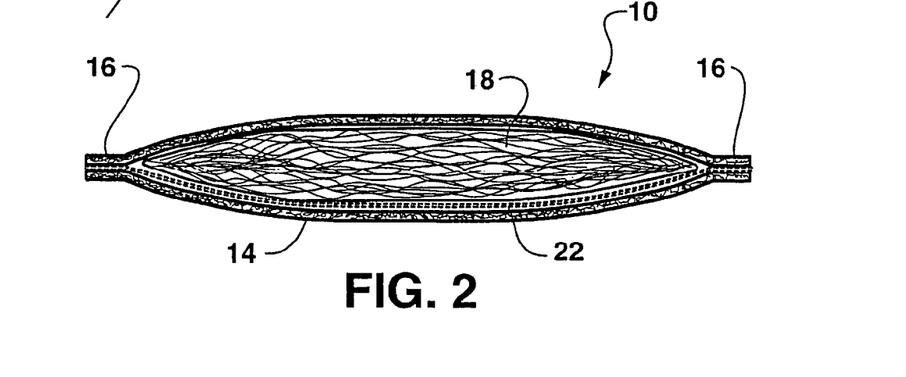
FIG. 2 is a cross-sectional view of the article of FIG. 1 taken along the lines indicated.
Figure 3:
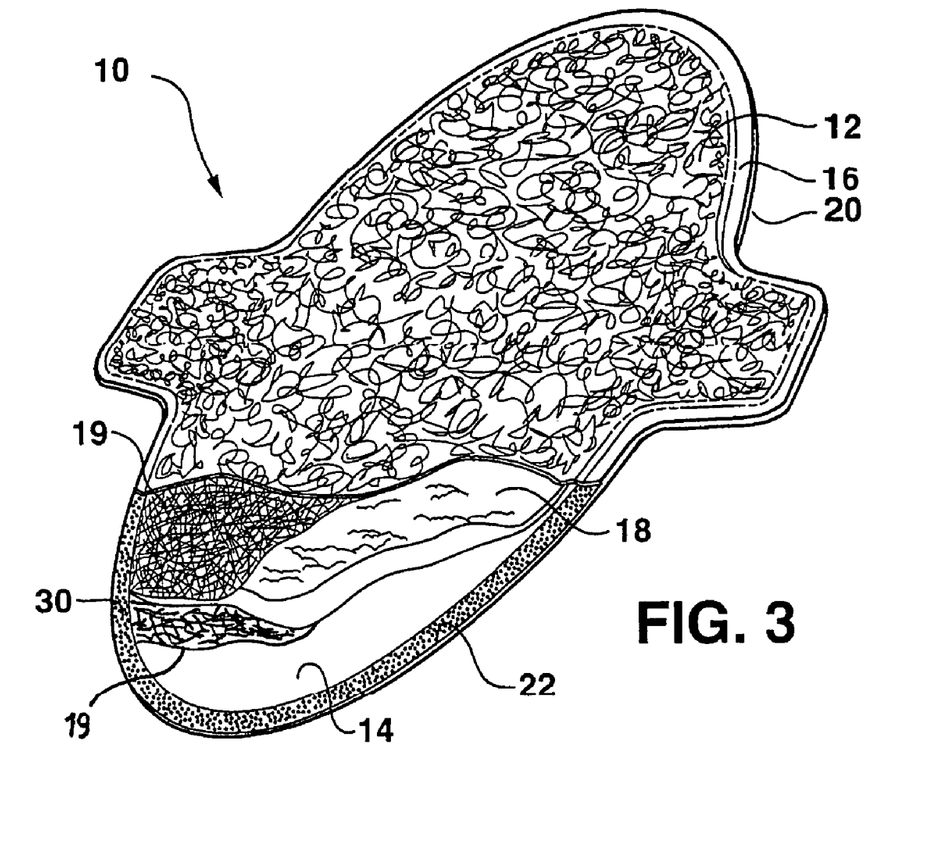
FIG. 3 is a perspective and partial cut-away view of an alternate embodiment of an interlabial absorbent article in accordance with the invention.

Referring to the figures in general, an embodiment of an interlabial absorbent article 10 is illustrated. The absorbent article 10 includes a cover sheet 12, a back sheet 14, and an absorbent material 18 sandwiched between the cover sheet 12 and back sheet 14. The cover sheet 12 and back sheet 14 are sealed together at their edges 16, the sealed edges 16 defining an overall circumference 20 and geometry for the article 10. The absorbent material 18 may extend to the circumferential edges of the article and be sealed with the cover sheet 12 and back sheet 14, or extend up to the seal 16 as shown in FIG. 2. The article 10 should be of a suitable size and shape which allows at least a portion, preferably a major portion, of the absorbent article to be disposed within the vestibule of a female wearer. In addition, the absorbent article 10 desirably at least partially occludes and intercepts the flow of menstrual fluid, urine or other bodily exudates from the wearer's vaginal orifice and/or urethral orifice.

As mentioned, the article 10 is not limited to any particular shape or configuration. In the illustrated embodiments, for example, the article 10 has an overall "butterfly" shape (oval with lateral tab portions). One skilled in the art will readily appreciate, however, that other geometries may also be suitable, including, for example, rectangular, ovoid-like, elliptical, trapezoidal, circular-like, triangular, square-shaped, teardrop-shaped, diamond-shaped, butterfly, pear-shaped, heart-shaped or a variety of combinations thereof. In addition, tabs or wings may be used with any of the overall geometries. Non-limiting examples of shapes for the tab include, ovoid, elliptical, trapezpoidal, rectangular, triangular, diamond-shaped, circular, semi-circular, or any combination of the above.

Although not illustrated in the figures, it should be appreciated that the article 10 may also include an insertion tab provided on the back sheet 14 to aid a user in placement of the article. This tab may be formed, for example, by a folded portion of the back sheet material that is bonded along a longitudinal seam to define a "flap" of material extending generally transversely from the plane of he back sheet 14, the flap being of a size for grasping by the user and constructed of any suitable material.

All or a portion of the components of the article 10 may be made of biodegradable materials.

The geometry of the absorbent material 18 is a significant factor affecting the overall size, shape, and effectiveness of the absorbent article 10. In general, the absorbent material 18 has a maximum width and a minimum width as measured in the transverse plane of axis B. For a circular or rectangular shaped article 10, the maximum and minimum widths are the same. In the embodiment of FIG. 1, the maximum width is defined at the transverse axis B and decreases towards the longitudinal ends of the article. The maximum width of the absorbent 18 typically is no greater than about 30 mm; alternatively, no greater than about 40 mm; alternatively, no greater than about 50 mm; alternatively, no greater than about 60 mm; or alternatively, no greater than about 70 mm. The minimum width of the absorbent 18 typically is no less than about 30 mm; alternatively, no less than about 20 mm; alternatively, no less than about 10 mm; or alternatively, no less than about 5 mm. Thus, the absorbent material 18 can have a width ranging from no less than about 5 mm up to no greater than about 70 mm; although the approximate width(s) of the absorbent can vary according to, inter alia, the general design and intended disposition of the absorbent article 10 within the vestibule of a female wearer.

The absorbent material 18 also has a maximum length measured along the principal longitudinal axis A of the article. The maximum length of the absorbent material 18 typically is no greater than about 40 mm; alternatively, no greater than about 50 mm; alternatively, no greater than about 60 mm; alternatively, no greater than about 70 mm; alternatively, no greater than about 80 mm; alternatively, no greater than about 90 mm; or alternatively, no greater than about 120 mm.

The absorbent article 10 is desirably provided with sufficient capacity to absorb and retain the intended amount and type of bodily exudate(s). The absorbent capacity is provided by a fluid retentive core made up of the absorbent material 18. The absorbent material 18 can have an absorbent capacity ranging from no less than about 1 g/g up to no greater than about 30 g/g; although the approximate capacity of the absorbent can vary according to, inter alia, the general design and intended disposition of the absorbent article 10 within the vestibule of a female wearer. One of skill in the art will readily realize that the addition of superabsorbent polymer or coated superabsorbent polymer) to the absorbent material 18 typically has the effect of substantially increasing the absorbent capacity.

Further, the size and absorbent capacity of the absorbent material 18 can be varied with the dimension, shape, and configuration of the absorbent material. For example, the absorbent can have a varying thickness with in the article 10, or can have a hydrophilic gradient, or can contain superabsorbent polymer(s) and the like. The flat absorbent material 18 will generally have a thickness of about 10 mm or less with a preferred flat thickness of about 2 mm and folded thickness of about 6 mm or less; although the approximate thickness of the absorbent can vary according to, inter alia, the general design and intended disposition of the absorbent article 10 within the vestibule of a female wearer With conventional interlabial articles, it has been observed that, upon flushing of such articles, gas bubbles are trapped between the low water vapor permeable substrates and the absorbent material. Trapping gas/water molecules between the cover and back sheet, without a method of escape, causes the product to have a positive buoyancy and thus to float to the surface. The products will stay positively buoyant beyond seven days unless external force or pressure pushes against the product to push the trapped air bubbles out of the product. Simulated septic tank laboratory tests showed that products with a permeable cover but back sheet that is impermeable to water and with a no/low vapor permeability tend to entrap large amounts of air, particularly between the absorbent material and the back sheet. In certain situations, the trapped air actually causes the back sheet to expand. The entrapped air bubbles create a product that is highly buoyant and, when tipped by water pressure or other sewage, immediately comes upright and regains equilibrium in the water. The high positive buoyancy of the product caused by entrapment of air prevents external forces from pushing the product over the tank baffle and into the second chamber of the septic tank because the article moves, tips, and regains balance easily on the surface of the water. The products can sink and go under the baffle if sufficient water pressure and/or particulate sewage is trapped on top of the product. However, this generally does not occur because high positive buoyancy results in easy tipping of the products thus preventing other materials from accumulating on and sinking the product As mentioned, the article 10 includes a unique combination of materials forming the cover sheet, back sheet, and absorbent material to produce buoyancy and delayed sinking properties that result in safe transport of the intact article through plumbing and municipal systems. The articles have an initial neutral buoyancy and do not disperse or break apart during transport. Within about 7 days after being flushed, the articles preferably sink, thus minimizing chances of the product becoming clogged in septic tanks and from becoming visible in water treatment plants or requiring removal from treatment plants.

With articles 10 according to the present invention, the initial neutral buoyancy characteristic is believed to be a result of a unique permeability relationship between the back sheet 14 and cover sheet 12. The cover sheet 12 preferably has a relatively high permeability to air and water vapor, while the back sheet is generally impermeable to liquids but has a generally high water vapor permeability. The cover sheet 12 can be constructed of any woven or nonwoven material which is easily penetrated by bodily fluids contacting the surface of the cover. Desirably, the cover sheet 12 has a water vapor permeability of at least about 30,000 Mocon value, or at lest about 50,000 Mocon value. Specific examples of suitable cover sheet materials are given below. Also, the back sheet 14 should have a water vapor permeability of at least about 20% of that of the cover sheet 12. The respective permeabilities are selected such that entrapped air may eventually escape from the article upon flushing regardless of the orientation of the article in the water. In this manner, the article is less likely to tip or turn over due to a high buoyancy mismatch between sides, as would be the case if entrapped air is retained between a vapor impermeable back sheet 14 and absorbent material 18. Also, the permeabilities are selected such that a sufficient volume of the entrapped air is initially retained in the article overall so as to provide the article with an initial neutral buoyancy. The entrapped air should escape at a rate such that the article eventually sinks within about 7 days after flushing.

A suitable technique for determining the "breathability" of a material (the ability of the material to permit gases, such as water vapor, to pass therethrough) is a test for the water vapor transmission rate (WVTR) value of the material as standardized by INDA IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR." The INDA procedure provides for the determination of WVTR, the permeance of the film to water vapor and, for homogeneous materials, water vapor permeability coefficient. The INDA test method is known to those skilled in the art and need not be set forth in detail herein. However, the test method is summarized as follows: A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion sell in which the test film is sealed. The sample holder is known as a Permatran-W Model 100 K manufactured by Mocon/Modem Controls, Inc., of Minneapolis, Minn. A first test is made of the WVTR of the guard film and air gap between an evaporator assembly that generates 100 percent relative humidity. Water vapor diffuses through the air gap and the guard film and then mixes with a dry gas flow which is proportional to water vapor concentration. The electrical signal is routed to a computer for processing. The computer calculates the transmission rate of the air gap and guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR.^{-1}{}_{test\ material} = TR^{-1}{}_{test\ material,\ guardfilm,\ airgap} - TR^{-1}{}_{guardfilm,\ airgap}$$

Calculations:

WVTR: The calculation of the WVTR uses the formula:

$$WVTR = F\rho_{sat}(T)RH/Ap_{sat}(T)(1-RH))$$

where:
F=The flow of water vapor in cc/min.,
$\rho_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

WVTR is measured in units of grams of water per square meter of material per 24 hours ($g/m^2$-24 hrs) ("Mocon" units).

A suitable technique for determining liquid permeability of a material in accordance with the present invention is set forth in Federal Test Method Standard FTMS 191 Method 5514, 1978, or an equivalent thereof.

A suitable technique for determining air permeability of a material in accordance with the present invention is with a Frazier Air Permeability Tester (Frazier Precision Instrument Co., Gaithersburg, Md.) and Method 5450, Federal Test Methods Standard No. 191A.

It has also been found that the difference in wettability between the cover sheet 12 and back sheet 14 may have a strong influence on the article's ability to sink. It is known that the rate of penetration of a liquid through a porous substrate is directly proportional to the cosine of the contact angle that the liquid makes with the surface of the substrate. The contact angle is thus a measure of the material's hydrophilicity gradient. A material's contact angle may be determined in accordance with ASTM D724-89. The present applicant has found that articles 10 having cover sheet and back sheet materials with similar contact angles have a greater probability of sinking by about 7 days from being flushed, as described in the following Example.

EXAMPLE

Interlabial absorbent articles were made (10 samples) with a cover sheet of a spunlace laminate material of rayon and PET/PP film having a Mocon value of about 39,947 and a basis weight of 30 gsm, and a back sheet of XEM 244 film (0.75 mil.) treated with PEG 400 (polyethylene glycol at a 0.5% add on level). The absorbent material was a blended layer consisting of 60% cotton and 40% rayon. The treated XEM 244 film has a contact angle with water between about 100 to 120 degrees. The rayon side of the cover sheet has a contact angle with water of between about 40 to 45 degrees. The film side of the cover sheet has a contact angle with water of between about 90 to 100 degrees. Articles were made with the cover sheet having the rayon side as the top (outward)

surface. Separate articles were made with the cover sheet having the film side as the top (outward) surface. The sets of articles were otherwise identical. The articles were separately tested in the flush test as set forth below. The articles having the rayon top surface had a sinking rate of approximately 30%. The articles having the film top surface had a sinking rate of about 70% during the test period.

Applicant believes that a contact angle mismatch between the cover sheet 12 and back sheet 14 of not greater than about 25% will significantly increase the probability that the article will sink within about 7 days from flushing.

To ensure that the article 10 eventually sinks, the absorbent material 18 may have a density greater than the sewage effluent (assumed to be water for purposes of this description). Thus, as the entrapped air providing the article 10 with its neutral buoyancy escapes, the weight of the article and density of the absorbent material will ensure that it sinks. In alternate embodiments, the absorbent material may have density less than water, but a wet weight (after absorption of its designed capacity) greater than water.

The absorbent material 18 can include any material capable of absorbing and/or adsorbing and thereafter retaining the intended bodily exudate(s). Suitable materials are also generally hydrophilic, compressible and conformable. The absorbent material 18 can be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester fibers and polypropylene fibers, absorbent foams, absorbent sponges, superabsorbent polymers, coated superabsorbent polymers, fibrous bundles or nits, or any equivalent material or combination of materials. Hydrophobic materials are also suitable for use where the hydrophobic material has been rendered hydrophilic according to any of a number of known methods for so doing.

The absorbent material 18 can have a basis weight of about 600 gsm or less; with a preferred basis weight of about 250 to about 400 gsm; although the approximate basis weight of the absorbent can vary according to, inter alia, the general design and intended disposition of the absorbent article 10 within the vestibule of a female wearer.

A specific example of a suitable absorbent is a coform material made of a blend of polypropylene and cellulose fibers such as that used in KOTEX brand pantiliners and obtainable from Kimberly-Clark Corporation, Neenah, Wis., USA.

In a particular embodiment of the article 10 in accordance with the invention, the absorbent material 18 is dispersible in water. Cellulosic fiber webs are generally considered dispersible in water in that they readily fragment into individual fibers upon sufficient exposure to an aqueous environment. Various other water dispersible absorbent materials are known to those skilled in the art and may be used with the present invention. For example, U.S. Pat. Nos. 5,952,251 and 5,948,710, such patents incorporated herein by reference for all purposes, describe absorbent dispersible coform materials that may be suitable for the present invention. U.S. Pat. No. 6,171,292 B1, incorporated herein by reference for all purposes, also discloses a number of dispersible absorbent materials that may be used with the present invention.

In particular embodiments, the absorbent material may be wrapped in a layer of material 19 which may be, for example, a tissue layer or soluble polymer layer, as seen in FIG. 3. Alternately, the layer 19 may be disposed only between the absorbent material 18 and cover sheet 12, or only between the absorbent material 18 and back sheet 14. In a particular embodiment, the material 19 is disposed between the absorbent material 18 and back sheet 14 with the water soluble adhesive or a water insoluble adhesive between the layer 19 and back sheet 14.

The fluid permeable cover sheet 12 has an outwardly facing surface that may contact the body of the wearer and receive bodily exudate(s). The cover sheet 12 desirably is made of a material which is flexible and non-irritating to the tissues within the vestibule of a female wearer. As used herein, the term "flexible" is intended to refer to materials which are compliant and readily conform to the bodily surface(s) with which such materials are in contact, or materials which respond by easily deforming in the presence of external forces.

The cover sheet 12 is provided for comfort and conformability and functions to direct bodily exudate(s) away from the body, through the cover sheet 12 and toward the absorbent material 18. The cover sheet 12 should retain little or no liquid in its structure so that the cover provides a relatively comfortable and non- irritating surface next to the tissues within the vestibule of a female wearer. The cover sheet 12 can be constructed of any woven or nonwoven material which is easily penetrated by bodily fluids which contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable cover material is a bonded carded web made of polypropylene and polyethylene such as that used as cover stock for KOTEX® pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures (not shown) formed therein which are intended to increase the rate at which bodily fluid(s) can penetrate through the cover and into the absorbent material 18.

A physiologically hydrous cover sheet material is also suitable for use. As used herein, the phrase "physiologically hydrous" is intended to connote a sheet material which maintains a suitably moist interface between the tissues of the vestibule and the absorbent article 10 when disposed in the vestibular environment; material which is benign respecting the requirements of comfort associated with the interposition of fabric or fabric-like structures within the moist tissue environment of the vestibule, also considering that the absorbent article receives bodily fluid(s) migrating through the vestibule and conducts such fluids to the absorbent material 18. Thus, while the cover sheet 12 is not "hydrous" in the classic sense prior to use, inasmuch as the sheet is dry at that time, the cover sheet 12 maintains, or at least does not interfere with the maintenance of, the proper moisture level or moisture balance required within the vestibule for proper maintenance of tissue health within the vestibule.

At least a portion of the surface of the cover sheet 12 can be treated with a surfactant in order to render the cover more hydrophilic. This results in permitting the insulting bodily fluid(s) to more readily penetrate the material The surfactant can also diminish the likelihood that the insulting bodily fluid(s), such as menstrual fluid, will flow off the cover sheet 12 rather than passing through the cover and being absorbed by the absorbent material 18. One suitable approach provides for the surfactant to be substantially evenly distributed across at least a portion of the upper surface of the cover sheet 12 which overlies the upper surface of the absorbent material 18.

The cover sheet 12 may also be embossed with any desired embossing pattern. Embossing techniques are well known to those skilled in the art. An embossing pattern not only creates an aesthetically pleasing surface, but the resulting embossed channels facilitate intake of menses fluid. Menses will tend to flow along the densified edges of the channels rather than pool on contact points of the cover sheet 12.

The cover sheet 12 can be maintained in secured relation with the absorbent material 18 by adhering all or a portion of the adjacent surfaces to one another with any pattern of an adhesive 22. The adhesive 22 may be a water insoluble adhesive, or an adhesive that becomes soluble after time, for example after about 7 days. Alternatively, portions of the cover sheet 12 may be fused or bonded to the adjacent surface of the absorbent material 18 and/or back sheet 14 by conventional bonding methods.

A suitable cover sheet material may have a water vapor transmission rate (WVTR) of at least about 30,000 Mocon value. For example, the cover sheet may be the spunlace material described above having a Mocon value of about 40,000, more particularly a value of 39,947. In an alternate embodiment, the cover sheet may have a Mocon value of at least about 50,000 Mocon value and may be, for example, a bonded carded web material.

The back sheet 14 typically resides on the lower surface of the absorbent material 18 as the absorbent article 10 is worn by a wearer, and can be constructed from any desired material which may be generally liquid-impermeable and water vapor permeable. Desirably, the back sheet 14 has a water vapor permeability of at least about 10,000 Mocon. Also, the back sheet 14 may have a water vapor permeability of at least about 25% of that of the cover sheet 12. In certain embodiments, the back sheet 14 may be permeable to liquid. Desirably, the back sheet 14 permits passage of air and moisture vapor out of the absorbent 10 while blocking passage of bodily fluid(s). An example of a suitable material is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render such fabrics liquid-impermeable. An example of another suitable material is a closed cell polyolefin foam, for example, a closed cell polyethylene foam. A specific example of a back sheet material is a polyethylene film such as that used in KOTEX pantiliners and obtainable from Pliant Corporation, Schaumburg, Ill., USA.

A particularly well suited material for the back sheet 14 is a highly breathable stretch thermal laminate (HBSTL) material having a Mocon value of at least about 10,000, more particularly a value of 10,824. The HBSTL material can include a polypropylene spunbond material thermally attached to a stretched breathable film. For example, the HBSTL material may induce a 0.6 osy (20.4 g/m$^2$) polypropylene spunbond material thermally attached to a 18.7 g/m$^2$ stretched breathable film. The breathable film may include two skin layers with each skin layer composed of 1-3 wt % EVA/catalloy. The breathable film may also include 55-60 wt % calcium carbonate particulates, linear low-density polyethylene, and up to 4.8% low density polyethylene. The stretched breathable film can include a thickness of 0.45-0.50 mils and a basis weight of 18.7 g/m$^2$. The spunbond layer can be thermally bonded to the breathable film, and can have a basis weight of 20.4 g/m$^2$. The spunbond layer can have a fiber denier of 1.5-3 dpf, and the stretched breathable film can be thermally attached to the spunbond material using any desired pattern which provides an overall bond area of at least about 15-20%.

The back sheet 14 can be maintained in secured relation with the absorbent material 18 by application of the adhesive 22 applied in any desired pattern between the backsheet 14 and absorbent material 18. The materials may be secured by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

The cover sheet 12 and back sheet 14 have periphery edges joined together to form a sealed circumferential edge 16 around the circumference 20 of the article 10. The adhesive 22 may be used to seal the edges of the cover sheet 12 and back sheet 14. In the embodiment illustrated in FIGS. 1 and 2, the adhesive 22 is applied generally uniformly over the inner surface of the back sheet 14 so as to extend generally completely to the edge of the sheet 14. The absorbent material structure 18 is slightly smaller than the dimensions of the back sheet 14 and cover sheet 12 and thus a circumferential border 30 of the adhesive combination 22 is defined. The cover sheet 12 is adhered to the back sheet 14 at this border to define a sealed edge 16 of the article 10. Although not illustrated in the figure, it should be appreciated that the adhesive 22 may also be used to join the cover sheet 12 to the absorbent material 18, as described above.

In an alternate embodiment of FIG. 3, the adhesive 22 is applied generally only as a circumferential band 30 and is intended primarily to join the cover sheet 12 and back sheet 14 around the sealed edges 16 of the article.

The following Test Protocol describes a method that may be used to determine the initial buoyancy and sinking characteristics of an interlabial absorbent article after being dropped into a toilet and flushed.

Test Procedure

This protocol measures the ability of Interlabial pads to clear a toilet fixture and in-house plumbing and allows visual observation of the product over time.

Sample flushing is done using a Kohler 1.6-gallon low water flow fixture and a 4" in-home piping system with approximately 35 feet of clear pipe area for product flow observations. The in-home piping system is designed using clear plastic pipe in 8 feet sections joined by standard 4" PVC fittings. The system is set-up to conform to minimum design standards from the Universal Plumbing Code and BOCA code for wastewater flow.

Water and product movement is supported by gravitational force on the waste products. The piping system also has a flow valve to allow water to be introduced into the piping to clear clogged or stranded materials from the flush test.

The protocol involves placing individual interlabial pads into a fixture bowl (pads only, no toilet paper or simulated feces) and evacuating the bowl with 1.6 gallons of water. The pad must completely clear the fixture with an internal water trap without clogging the flow of the water and waste as it moves to the delivery piping. There should be no residual accumulation of the product in any of the system components.

After flushing and collecting the pads, they are transferred to a container of water for observation at 4 hours, 24 hours, and 7 days.

Equipment

Fixture—KOHLER toilet; low water flow 1.6 gallon

In-home Piping System—4" clear plastic pipe (polycarbonate)

Collection screen—Stainless steel ¼" mesh or multi level sieve screen

Plastic container with lid (STERLITE container 28 qt., 23¼ in.×17 in.×6 in.) Note: The minimum dimensions of the container are important. There must be enough room for all of the pads to float without touching each other or the sides of the container. The water depth needs to be a minimum of 1½ inches greater than the products' length.

Plastic white 8" stir stick

Sampling and Test Procedure

All pads from each code (sample) should be tested in the same day.

Ensure that the containers are clean by wiping them out with a clean, dry cloth after each 7 day test. Do not use detergent or soap to clean the containers as it may affect the test results.

1) Select a code for testing and number each pad on both sides (cover and baffle).

2) Fold pad in half lengthwise, cover side out. Place the folded pad between the index and middle finger. With arm resting on the toilet seat, open fingers to drop 1 pad into the bowl. Note if it lands cover up or cover down. Wait for 30 seconds, then flush. Note if the product does not clear the bowl on the first flush. If necessary, flush a second time to clear the product from the bowl.

3) Repeat step 2 until 10 pads are flushed.

4) Inspect the collection screen to ensure that all the pads were collected. If any of the pads became entrapped in the system, add more water to the system by flushing or opening a valve to drive out the pads that did not initially clear the system. Note the number and location of the pads that were entrapped in the system.

5) Add water, from the collection tank, to the container to fill it ½ inch from the top (=5½ inch water level). Ensure that containers have been wiped clean before starting.

6) Visually inspect each pad and transfer it to the container to which water had previously been added. Note which pads if any, had open seals, location of the open seals or if the product is coming apart in any way. When transferring pad to container, position the pad horizontally (cover side up on even # pads and baffle side up on odd # pads), grasp the pad in the center with thumb and finger, submerge the pad halfway below the surface of water then let go of pad. Place all pads from the same code in one container. [Exception for large size: only place 15 pads in one container]. Label the container with the product code and time when pads were added. Put lid on the container.

7) Repeat steps 1-6 until all pads from the same code have been flushed.

8) 3½ hours to 4½ hours (if the time exceeds 4½ hours make a notation on the data sheet) after placing the last set of 10 pads of the same code in the container gently stir the pads 5 times with a plastic stir stick, wait 5 minutes. Note the number of pads still floating and the buoyancy of the pads, the extent to which the pads have separated into individual components, or the extent of seal separation between the cover sheet and back sheet.

9) 23½ hours to 24½ hours (if the time exceeds 24½ hours make a notation on the data sheet) after placing the pads in the container, gently stir the pads 5 times with a plastic stir stick, wait 5 minutes, and note the number of pads still floating, the buoyancy of the pads, and any other visual assessments, including the extent to which the pads have separated into individual components.

10) 7 days after placing the pads in the container, gently stir the pads 5 times with a plastic stir stick and wait 5 minutes. Note the number of pads still floating and the extent to which the pads have separated into individual components or the extent of seal separation between the cover sheet and back sheet. Note the location of the open seals and if the pads appear to have air trapped inside of them.

11) Pads may be saved for later inspection.

EXAMPLE

Two separate codes of interlabial absorbent articles were made (10 samples per code) and tested in accordance with the procedure set forth above. The articles measured 79 mm long by 69 mm wide.

First Code: Articles included an absorbent layer of 70% cotton and 30% rayon with a density of about 1.37 g/cc. The cover sheet was a bonded carded web (BCW) material having a WVTR of about 52,612 Mocon value, an air permeability of about 762 cfm/ft$^2$ (cubic feet per minute per square foot), and a contact angle with water of between about 70-80 degrees. The back sheet material comprised an HBSTL material (as described above) having a WVTR of about 10,824 Mocon value, an air permeability of about 5 cfm, and a contact angle with water of between about 85-100 degrees. All pads were successfully flushed without dispersing or breaking-up and their buoyancy and sinking characteristics noted at the times set forth in the above procedure. The pads generally exhibited neutral buoyancy during flushing in that they tended not to flow on top of the water stream, but rather between the bottom of the piping and the top of the water stream. Also, upon being placed in the container after the flush test, the articles were generally suspended at various positions in the container and did not rise and float on the surface. 60% of the pads tested completely sank within 7 days.

Second Code: Articles included an absorbent layer of 60% cotton and 40% rayon with a density of about 1.2 g/cc. The cover sheet was a spunlace laminate material of rayon and PET/PP film with the film side facing out, as described above, a WVTR of about 39,947 Mocon value, an air permeability of about 0.76 cfm, and a contact angle with water (film side out) of between about 90-110 degrees. The back sheet material comprised an HBSTL material (as described above) having a WVTR of about 10,824 Mocon value, an air permeability of about 5 cfm, and a contact angle with water of between about 85-100 degrees. All pads were successfully flushed without dispersing or breaking-up and their buoyancy and sinking characteristics noted at the times set forth in the above procedure. The pads generally exhibited neutral buoyancy during flushing in that they tended not to flow on top of the water stream, but rather between the bottom of the piping and the top of the water stream. Also, upon being placed in the container after the flush test, the articles were generally suspended at various positions in the container and did not rise and float on the surface. Between 95-100% of the pads tested completely sank within 7 days.

It should be appreciated by those skilled in the art that various modifications and variations may be made to the embodiments of the invention illustrated or described herein without departing from the scope and spirit of the invention as set forth in the appended claims and their equivalents.

What is claimed is:

1. An interlabial absorbent article configured for disposition primarily within the vestibule of a female wearer, comprising:
- a generally liquid permeable, non-apertured cover sheet comprising a first material;
- a generally liquid impermeable back sheet comprising a second material, said second material different from said first material;
- an absorbent material disposed between said cover sheet and said back sheet;
- wherein said back sheet has a water vapor transmission rate that is at least about 20% of a water vapor transmission rate of said cover sheet, up to a water vapor transmission rate of about 50,000 g/m$^2$-24 hrs;
- wherein said cover sheet and said back sheet have a contact angle mismatch of less than about 25%; and
- wherein upon being flushed, said article has an initial neutral buoyancy and subsequently sinks within about 7 days from being flushed.

2. The interlabial absorbent article as in claim 1, wherein said cover sheet has a water vapor transmission rate of at least about 30,000 g/m$^2$-24 hrs to about 50,000 g/m$^2$-24 hrs.

3. The interlabial absorbent article as in claim 2, wherein said cover sheet comprises a spunlace laminate material of rayon and film.

4. The interlabial absorbent article as in claim 2, wherein cover sheet comprises a bonded carded web material having water vapor transmission rate of about 52,000 g/m$^2$-24 hrs.

5. The interlabial absorbent article as in claim 1, wherein said back sheet comprises a HBSTL material having a water vapor transmission rate of about 10,000 g/m$^2$-24 hrs.

6. The interlabial absorbent article as in claim 1, wherein said cover sheet has a water vapor transmission rate of about 40,000 g/m$^2$-24 hrs and said back sheet has a water vapor transmission rate of about 10,000 g/m$^2$-24 hrs.

7. The interlabial absorbent article as in claim 1, wherein said cover sheet has a water vapor transmission rate of about 50,000 g/m$^2$-24 hrs and said back sheet has a water vapor transmission rate of about 10,000 g/m$^2$-24 hrs.

8. The interlabial absorbent article as in claim 1, wherein said absorbent material has a dry density of about 1.0 g/cc.

9. The interlabial absorbent article as in claim 1, wherein said absorbent material has wet density of about 1.0 g/cc.

10. The interlabial absorbent material as in claim 1, wherein said cover sheet is adhered to said back sheet with an adhesive around a circumference of said article, and wherein said article does not separate into individual components for at least about 7 days after being flushed.

11. The interlabial absorbent article as in claim 1, wherein said absorbent material comprises a cotton/rayon blend.

12. An interlabial absorbent article configured for disposition primarily within the vestibule of a female wearer, comprising:
- a generally liquid permeable, non-apertured cover sheet having a water vapor transmission rate of at least about 30,000 g/m$^2$-24 hrs, to about 50,000 g/m$^2$-24 said cover sheet comprising a first material;
- a generally liquid impermeable back sheet comprising a second material, said second material different from said first material;
- an absorbent material disposed between said cover sheet and said back sheet;
- wherein said water vapor transmission rate of said back sheet is at least about 20% to about the same water vapor transmission rate of said cover sheet; and
- wherein upon being flushed, said article has an initial neutral buoyancy and subsequently sinks within about 7 days from being flushed.

13. The interlabial absorbent article as in claim 12, wherein said cover sheet and said back sheet have a contact angle mismatch of less than about 25%.

14. An interlabial absorbent article configured for disposition primarily within the vestibule of a female wearer, comprising:
- a generally liquid permeable, non-apertured cover sheet comprising a first material;
- a generally liquid impermeable back sheet comprising a second material, said second material different from said first material;
- an absorbent material disposed between said cover sheet and said back sheet;
- wherein said back sheet has a water vapor transmission rate that is at least about 20% to about the same water vapor transmission rate of said cover sheet; and
- wherein said absorbent material has a dry density of at least about 1.0 g/cc.

15. The interlabial absorbent article as in claim 14, wherein said cover sheet and said back sheet have a contact angle mismatch of less than about 25%.

16. The interlabial absorbent article as in claim 14, wherein said article has an initial neutral buoyancy such that said article sinks within about 7 days from being flushed.

* * * * *